(12) United States Patent
Houston

(10) Patent No.: US 6,319,479 B1
(45) Date of Patent: Nov. 20, 2001

(54) CLOSURE FOR A HINGED STERILIZER DOOR

(75) Inventor: John C. Houston, Erie, OH (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/257,117

(22) Filed: Feb. 25, 1999

(51) Int. Cl.[7] .................. A61L 2/00; A61L 9/00; E05B 63/00; E06B 3/00; E05C 3/06
(52) U.S. Cl. .............. 422/292; 70/105; 70/135; 109/59 R; 109/74; 292/47; 292/49
(58) Field of Search .................. 422/26, 28, 118, 422/292, 295; 220/232, 243, 248, 251, 314, 820, 821, 822, 323; 292/46, 47, 49, 197; 109/58.5, 59 R, 64, 74; 70/94, 102–105, 130–131, 135, 136

(56) References Cited

U.S. PATENT DOCUMENTS

| | | | |
|---|---|---|---|
| 4,261,189 | * | 4/1981 | Brumfield, Jr. et al. ............ 70/84 |
| 4,387,740 | * | 6/1983 | Vanzant ............................. 138/89 |
| 4,607,760 | * | 8/1986 | Roche ............................... 220/314 |
| 4,756,123 | | 7/1988 | Roche et al. . |
| 4,891,910 | | 1/1990 | Cook et al. ......................... 49/395 |
| 4,999,165 | * | 3/1991 | Calabra et al. .................... 422/113 |
| 5,148,938 | * | 9/1992 | Morgan, Jr. ........................ 220/316 |
| 5,711,450 | | 1/1998 | Reneau .............................. 220/319 |

FOREIGN PATENT DOCUMENTS

2218179A1    11/1989  (GB) .

* cited by examiner

Primary Examiner—Robert J. Warden, Sr.
Assistant Examiner—Monzer R. Chorbaji
(74) Attorney, Agent, or Firm—Fay, Sharpe, Fagan, Minnich & McKee, LLP

(57) ABSTRACT

A closure assembly (20) for engaging a door (14) across the opening (16) of a chamber (12) includes first and second triangular plates (28) and (30) which are pivotally connected to opposite corners of a front face (32) of the door. The plates face each other at the longest sides of the triangles. The remaining sides of the triangles define engagement portions (72, 74, 76, 78). To restrain the door, the plates are pivoted (50, 52) until the engagement portions engage flanges (80, 82, 84, 86) situated around the perimeter of the opening. A seal (96) is then activated to seal the door around the opening. Preferably, a coupling member (33) is coupled to the plates to coordinate their pivoting. Cam slots (114, 116), defined in the coupling member, receive followers (118, 120) connected to the two plates. An operator rotates the coupling member, the followers are cammed or permitted to move by gravity as the plates are pivoted apart and together.

22 Claims, 6 Drawing Sheets

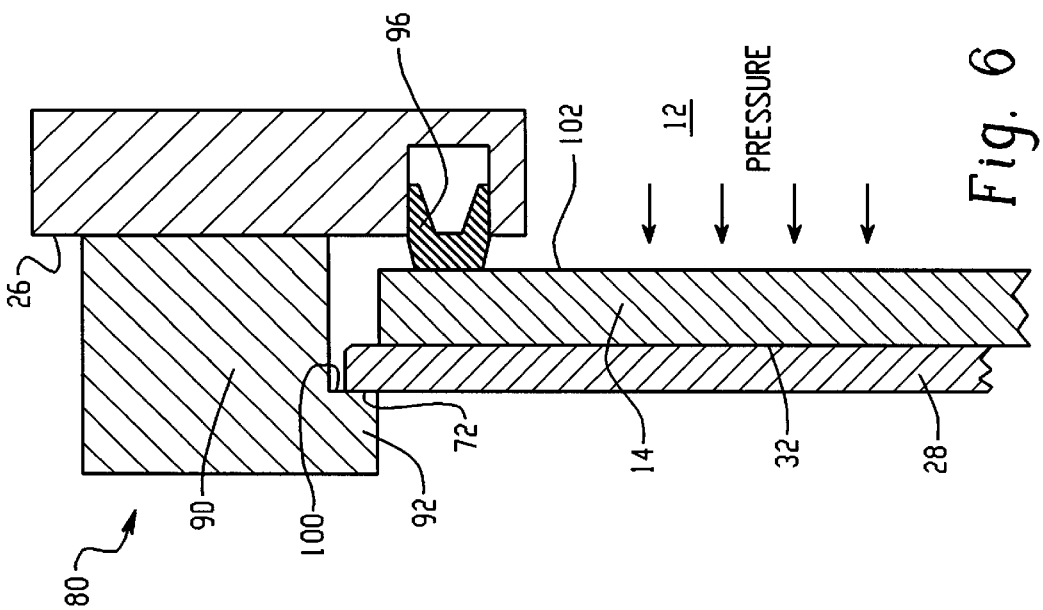
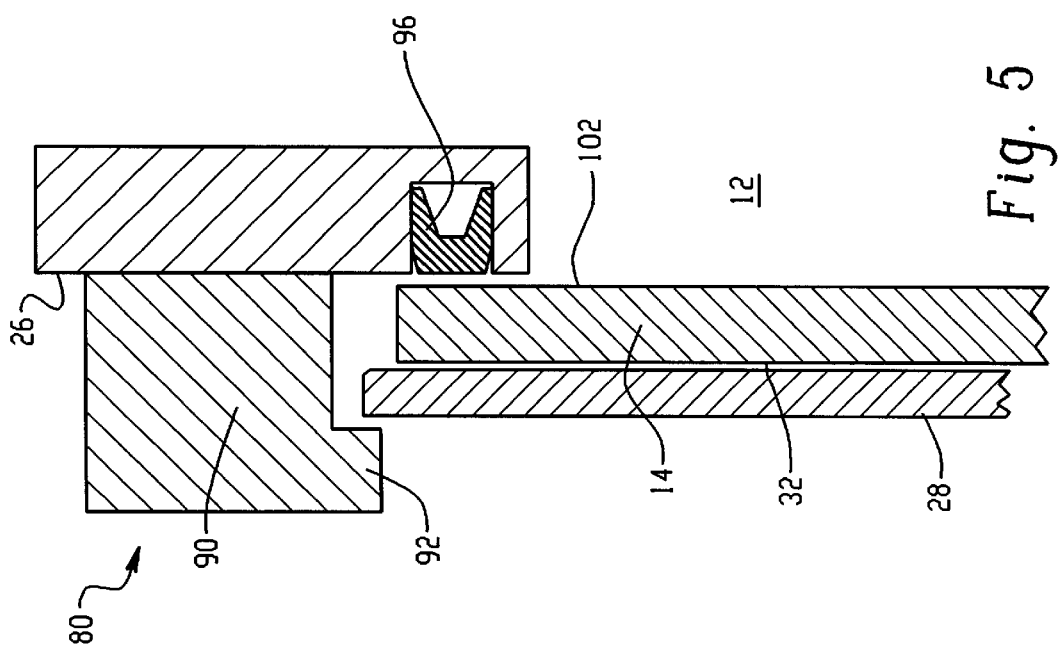

CLOSURE FOR A HINGED STERILIZER DOOR

BACKGROUND OF THE INVENTION

The present invention relates to the door closure arts. It finds particular application in connection with restraining a door across an opening to a steam sterilization chamber, and will be described with particular reference thereto. It should be appreciated, however, that the invention is also applicable to a wide variety of doors which are to be securely fastened to a pressure vessel or which are to be secured on four sides, such as vault doors or ship doors.

Conventionally, steam sterilizers are operated at high internal pressures and temperatures. To maintain these temperatures and pressures, the door of the sterilizer is generally clamped in position across an opening to the sterilization chamber by a closure assembly. Typically, a sterilization chamber door must be sealed to approximately 15 to 20 Kilograms force to prevent the door from leaking. A gasket or other flexible member is sealed between the door and the chamber. The closure assembly inhibits the ingress of air around the seal and also prevents hazards arising from accidental opening of the door during a sterilization cycle.

U.S. Pat. Nos. 4,756,123 and 4,891,910 disclose examples of closures for sealingly engaging a door across the opening to a sterilization chamber. U.S. Pat. No. 4,891,910 discloses a motorized closure assembly which drives a central locking wheel. A plurality of arms are connected to the locking wheel. The arms move upon rotation of the locking wheel until outer ends of the arms engage a plurality of apertures positioned along the perimeter of the opening to the chamber. Such closure assemblies are often complex, requiring a number of moving parts.

The present invention provides for a new and improved closure assembly for restraining a sterilizer door which overcomes the above-referenced problems and others.

SUMMARY OF THE INVENTION

In accordance with one aspect of the present invention, a steam sterilizer apparatus is provided. The apparatus includes a pressure chamber with a door frame which defines an opening into the chamber. A door is connected to the door frame and is sized to cover the opening. A plurality of flanges are connected with the door frame, at least one flange being adjacent each of opposite edges of the door. A closure assembly selectively maintains the door in a proximate relationship to the frame. The closure assembly includes first and second plates. The first plate has an uppermost portion which is pivotally connected to the door and an engagement portion which is pivoted into and out of engagement with one of the flanges. The second plate has a lowermost portion which is pivotally connected to the door and an engagement portion which is pivoted into and out of engagement with another of the flanges.

In accordance with another aspect of the present invention, a closure assembly f or selectively maintaining a door in sealing engagement around an opening in a cabinet is provided. Flanges extend from a front face of the cabinet. The assembly includes first and second plates, pivotally connected adjacent first and second sides of the door, respectively. The first and second plates each define two engagement portions for selectively engaging two of the flanges. A coupling member couples the first plate to the second plate for selectively rotating them from a disengaged position, in which the engagement portions are displaced from the flanges, to an engagement position, in which the engagement portions engage the flanges.

In accordance with yet another aspect of the present embodiment, a method of selectively restraining a door across an opening is provided. The method includes pivoting first and second plates which each define two engagement portions until the engagement portions engage corresponding flanges. The two plates are pivotally connected to the door.

One advantage of the present invention is that it requires few moving parts.

Another advantage of the present invention is that the closure may be operated with application of minimum operator effort and a minimum of articulation.

Another advantage of the present is that the closure is self-locking in the engaged position.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 6 is a side sectional view along Section A—A of FIG. 4 with the flange engaged and the seal actuated; and, FIG. 7 is a front elevational view of the closure assembly of FIG. 1 in both the engaged (hatched lines) and disengaged (solid lines) positions.

DETAILED DESCRIPTION OF THE PREFERRED EMBODIMENTS

Figure 1:
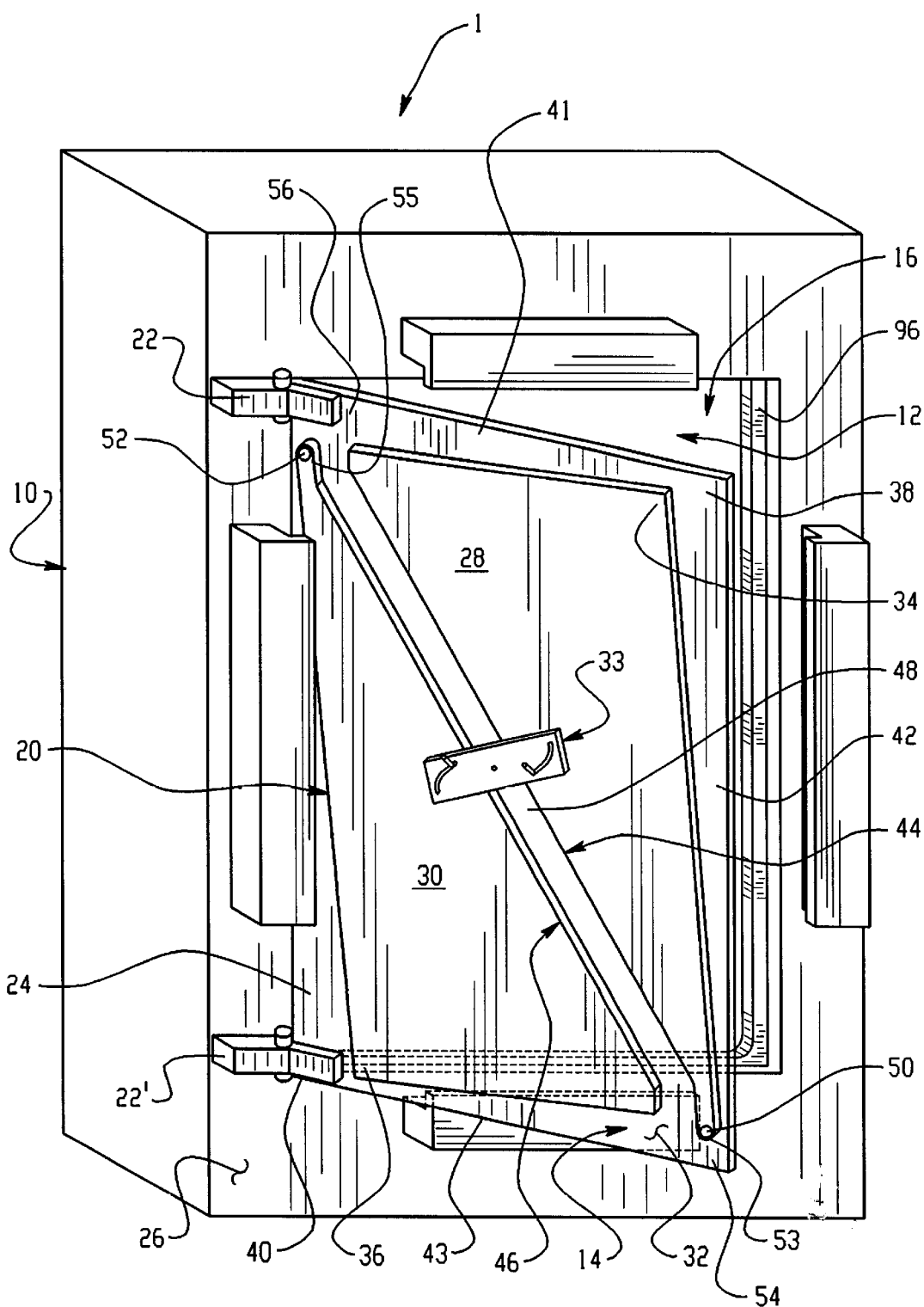
FIG. 1 is a front perspective view of a sterilizer with a cosmetic front door surface removed to show a counterbalanced closure assembly according to the present invention.

With reference to FIG. 1, a steam sterilization apparatus 1 includes a cabinet 10 which defines an interior chamber 12. A rectangular door 14 opens and closes to allow items to be sterilized to be loaded and unloaded into the chamber through an opening 16 in the chamber. The door is sized to cover completely the opening and is preferably formed from a material which is resistant to the chemical environment within the chamber, such as a stainless steel plate. When the door is in the closed position, a closure assembly 20 selectively restrains the door.

Hinges 22 pivotally connect a first vertical side or edge 24 of the door to a door frame, such as a frame or front wall 26 of the cabinet, which defines the opening. The hinges allow pivotal movement of the door during opening and closing. The hinges also permit a small amount of transverse motion of the door in a direction perpendicular to the front wall of the cabinet to allow a small door movement due to pressure changes within the sterilizer.

The closure assembly 20 includes two generally triangular-shaped flat plates of substantially equal weight, namely an upper plate 28 and a lower plate 30, which are pivotally mounted to a flat exterior face 32 of the door, and a coupling member 33 for articulating the plates from a disengaged position, in which the door 14 can be opened, to an engaged position, in which the door is restrained in position across the opening 16.

The plates 28 and 30 are formed from a rigid material, such as steel, and are of a sufficient thickness, e.g. 1–2 cm, to withstand the pressures exerted on the door from within the chamber 12. Each of the plates has a generally right-angled corner 34 and 36, respectively, which is indented, as will be described in further detail hereinafter. The two right-angled corners are positioned adjacent diagonally opposite corners 38 and 40, respectively, of the door. Specifically, the door first upper corner 38 is defined between the top of the door 41 and a second vertical side or edge 42 of the door that is furthest from the hinges and the first lower door corner 40 is defined between the bottom of the door 43 and the first vertical edge 24 of the door. The upper plate 28 is thus positioned with its right-angled corner 34 adjacent the first upper corner 38 of the door, and the lower plate is positioned with its right-angled corner 36 adjacent the first lower corner 40 of the door. The plates are arranged so that their longest sides 44 and 46, respectively, lie parallel to each other, in facing opposition and generally diagonally across the door. A gap 48 is preferably defined between the two plates.

The plates are pivotally connected to the exterior face 32 of the door of the sterilizer at plate pivot points 50 and 52, respectively, by any suitable pivoting means, such as a pivot pin. The pivot pins allow the plates to rotate in a plane parallel to the exterior face 32 of the door. The pivot points are located adjacent diagonally opposite corners of the door. Specifically, the pivot point 50 of the upper plate 28 is positioned adjacent a corner of the plate 53 closest to a second lower corner 54 of the door defined between the second edge 42 of the door and the bottom 43 of the door, while the pivot point 52 for the lower plate 30 is positioned adjacent a corner 55 of the plate which is adjacent a second upper corner 56 of the door, defined between the first edge 24 of the door and the top of the door 41.

While the shapes of the two plates 28 and 30 and their respective pivot points 50 and 52 have been described in relation to the first and second edges of the door 24 and 42, it is to be understood that the positions of the plates could also be flipped 180° so that one of the plates is positioned with its right-angled corner adjacent the second upper corner 56 of the first edge of the door and the other plate with its right-angled corner adjacent the lower corner 54 of the second edge of the door. It is to be understood that this alternative arrangement of the plates is also contemplated. Additionally, while FIG. 1 shows the door hinges on the left edge of the door, the door could equally well be hinged on the right of the door, or on the top or bottom of the door, if desired.

Figure 2:
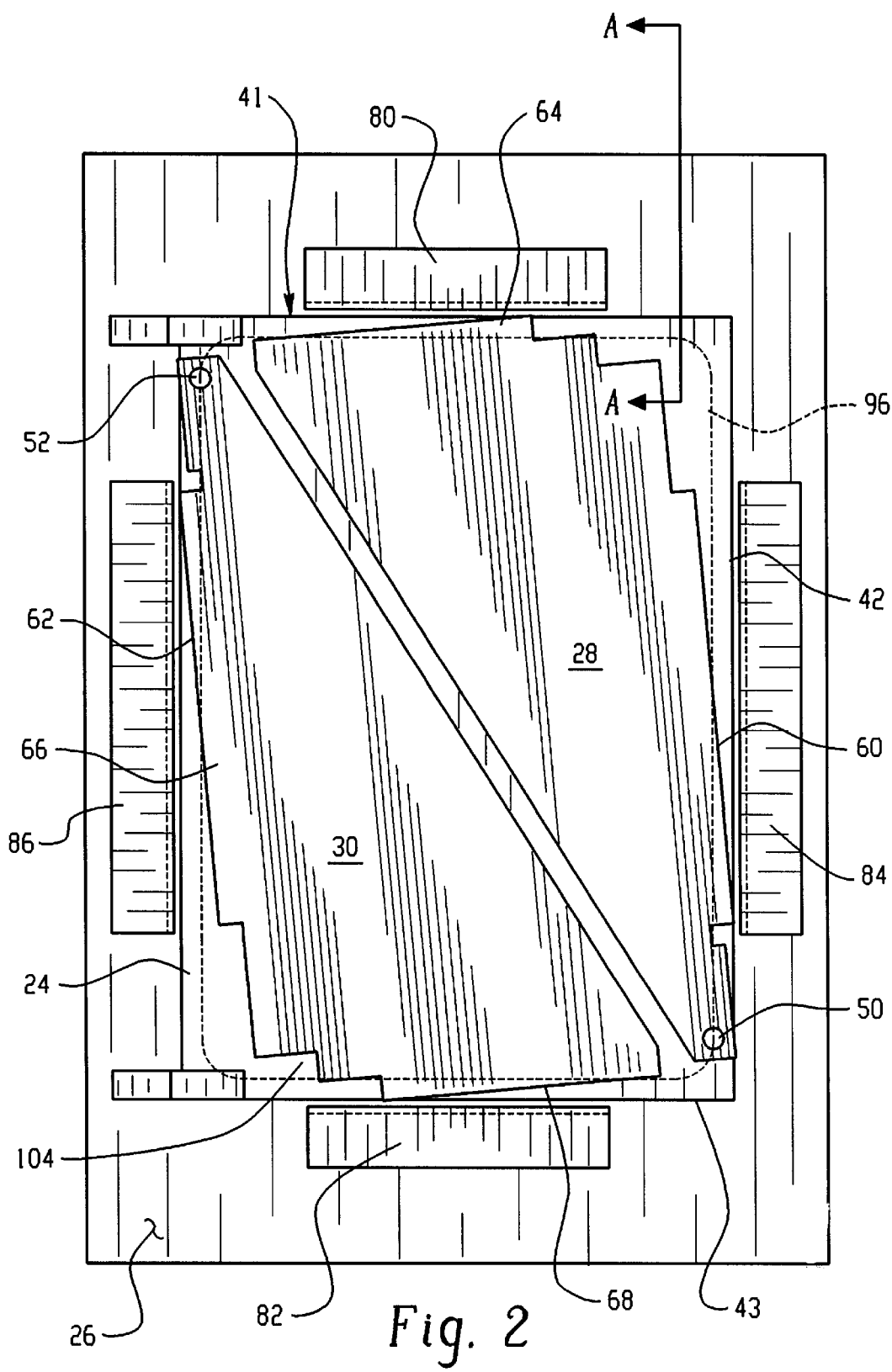
FIG. 2 is schematic front elevational view of a sterilizer door and closure assembly in the disengaged position, in accordance with the present invention.
Figure 3:
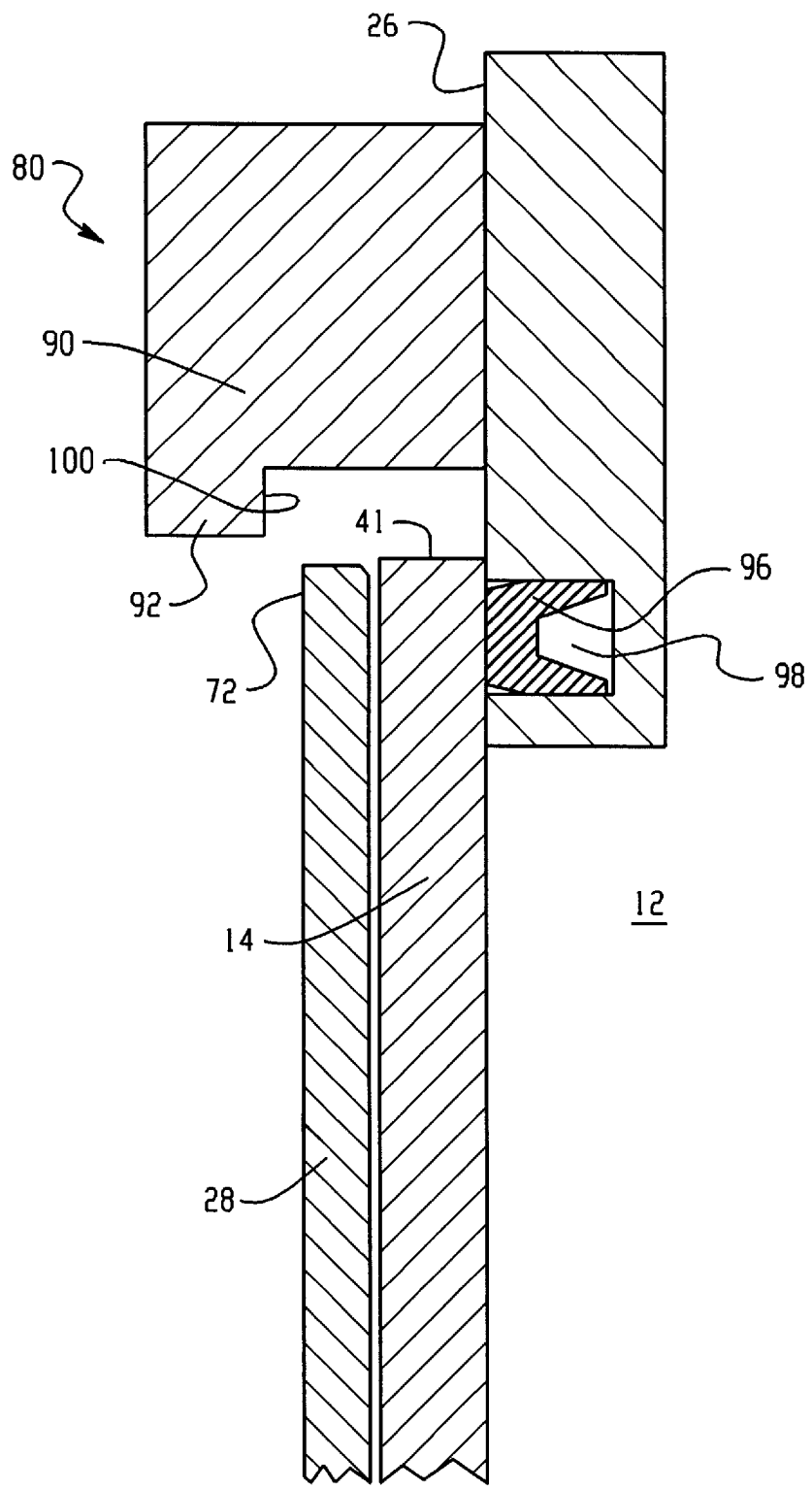
FIG. 3 is an enlarged side sectional view of the door and closure plate of FIG. 2 along Section A—A.

With reference also to FIGS. 2 and 3, the plates 28 and 30 are shaped and positioned so that in the disengaged position the periphery of the plates does not extend beyond the periphery of the door. As seen from FIGS. 1 and 2, in the disengaged position, the horizontal and vertical edges of the two plates are not aligned in parallel with the adjacent vertical and horizontal edges of the door, but rather are offset by a few degrees, preferably from about 5–15°. Specifically, the gap between a side edge 60 of the upper plate 28 and the adjacent second edge of the door 42 narrows from top to bottom of the door, while the gap between a side edge 62 of the lower plate 30 and the adjacent first edge 24 of the door widens from top to bottom of the door. Similarly, the gap between an upper edge 64 of the upper plate 28 and the adjacent horizontal top 41 of the door narrows from the first edge 24 of the door to the second edge 42 of the door, while the gap between a bottom 68 of the lower plate 30 and the adjacent horizontal bottom 43 of the door widens from the first to the second edge.

Figure 4:
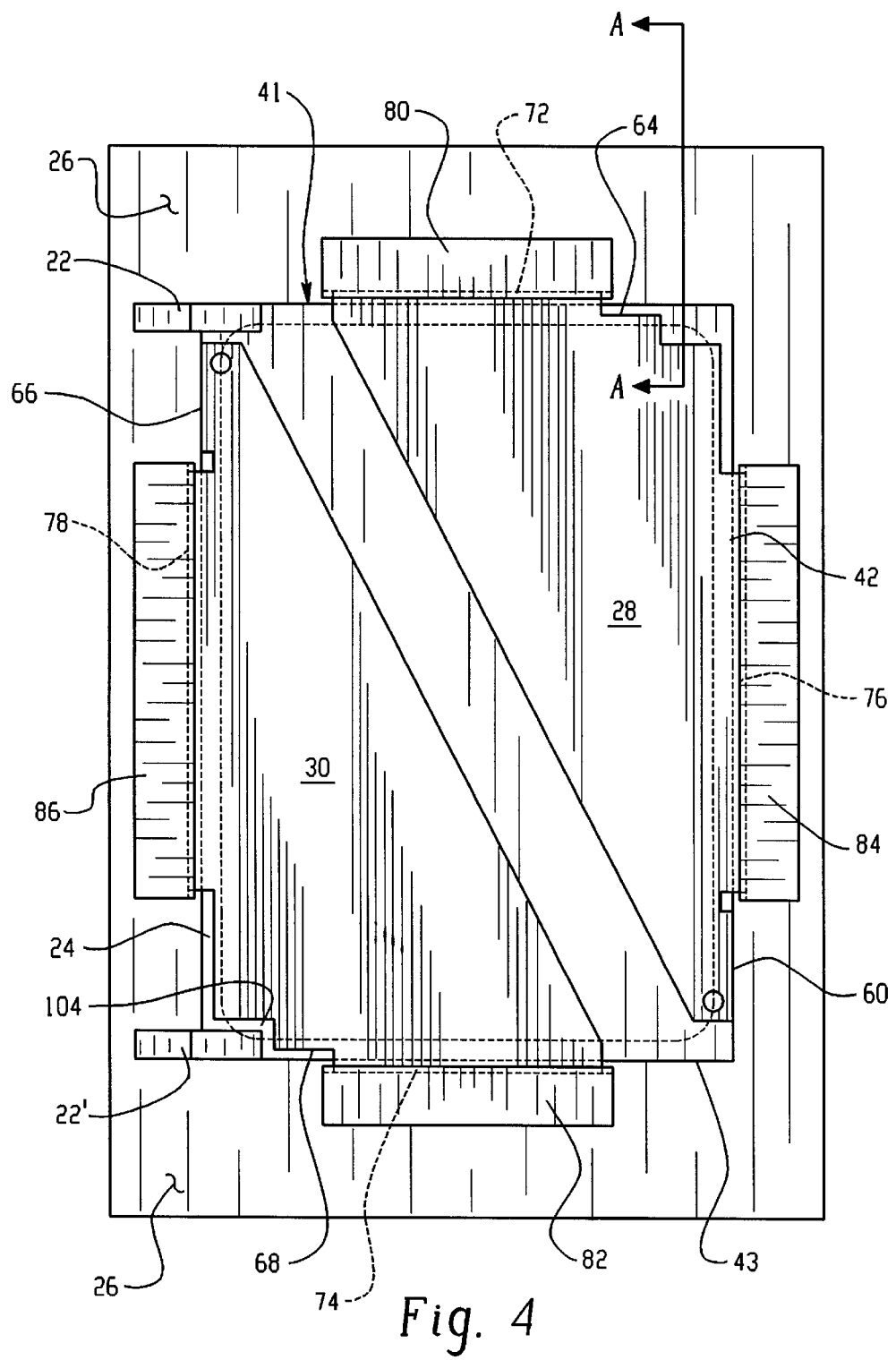
FIG. 4 is a front elevational view of the door and closure assembly of FIG. 2 in the engaged position, in accordance with the present invention; and, FIG. 5 is a side sectional view along section A—A of FIG. 4 with the flange engaged.

With reference also to FIG. 4, which shows the plates in the engaged position, the upper and lower and side edges of the two plates 64, 68, 60 and 66, respectively, define engagement portions. Specifically, a first engagement portion 72 is defined by the upper edge 64 of the upper plate 28, a second engagement portion 74 is defined by the lower edge 68 of the lower plate 30, a third engagement portion 76 is defined by the side edge 60 of the upper plate and a fourth engagement portion 78 is defined by the side edge 62 of the lower plate.

Four over-hanging retaining members or bars 80, 82, 84, and 86 are positioned around the perimeter of the opening 16. The retaining bars are rigidly connected with the front face 26, or structural frame of the sterilizer, adjacent to the corresponding four engagement portions 72, 74, 76, and 78. With reference also to FIGS. 3 and 5, each of the retaining bars 80, 82, 84, and 86 extends parallel to, and slightly spaced from, the adjacent edge of the door 41, 43, 42 and 44, respectively, so that the bars do not interfere with the opening and closing of the door. Each of the retaining bars includes a spacer portion 90 which extends beyond the exterior face 32 of the door to a position which is slightly forward of the corresponding plate engagement portion 72, 74, 76, and 78. (See FIG. 4.) On each bar, a flange 92 extends perpendicularly from the forward end of the spacer portion. The flange on the bar 80 also extends parallel to the top 41 of the door, while the flanges on the bars 82, 84, and 86 also run parallel to their respective edges 43, 42 and 24 of the door. The flange overlaps the corresponding engagement portion when the closure assembly 20 is in the engaged position, as shown in FIG. 5. Accordingly, each plate is engaged by two perpendicularly positioned flanges.

With particular reference to FIGS. 3, 5, and 6, a door seal, such as a gasket 96, is housed in a channel 98 which is defined in the front surface 26 of the cabinet and which extends around the perimeter of the opening 16. FIGS. 3 and 5 show the seal prior to activation. To activate the seal, the channel is supplied with steam, or other pressurizing fluid while the plates 28, 30 are in the engaged position. The seal moves outwardly from the channel, compressing the door 14 and the plate engagement portions 72, 74, 76, and 78 against an interior sealing face 100 on the corresponding flange 92, as shown in FIG. 6. A leak-tight seal is thus formed between an interior surface 102 of the door and the front surface 26 of the cabinet, thus sealing the opening to the chamber 12. The flanges 92 and engagement portions 72, 74, 76, and 78 cooperate to prevent the door from opening in response to a pressure from within the chamber.

To move the closure from the disengaged to the engaged position and seal the door 14 across the opening 16, the door is first pivoted from an open position, shown in FIG. 1, to a closed position, shown in FIG. 2, where the door is positioned generally parallel to the front surface 26 of the cabinet. The two plates 28 and 30 are rotated about their pivot points 50 and 52, in a clockwise direction. As the plates rotate, the engagement portions 72, 74, 76, and 78 of the plates are brought into engagement with the respective flanges 92 of the retainer bars 80, 82, 84, and 86. The plates are then in the positions shown in FIGS. 4 and 5. A cut-out portion 104 in the lower plate 30 is shaped to allow for the protrusion of the hinge 22. The upper plate 28 may be provided with a similar cut-out portion so that the plates may be operated on either a left opening or a right opening door. Additionally, it is desirable for the plates to be manufactured similarly so that they are of approximately equal or identical weight. Further, eliminating material along the top and bottom edges toward the corners can reduce the distance the plates move between the engaged and disengaged positions. Once the plates 28 and 30 are in position with the engagement portions engaged by the respective retainer bar flanges, the seal 96 is activated, as shown in FIG. 6.

In the engaged position, each edge of the door is restrained from outward movement by the engagement of the corresponding engagement portion and flange. While it is also contemplated that a single engagement portion be provided on each of the plates 28 and 30, rather than two engagement portions, the use of two engagement portions assists in restraining the door. Specifically, when an outward force is applied adjacent to a first engagement portion, the force will be distributed over the entire plate as the adjacent engagement portion resists pivoting of the plate around the first engagement portion.

Figure 7:
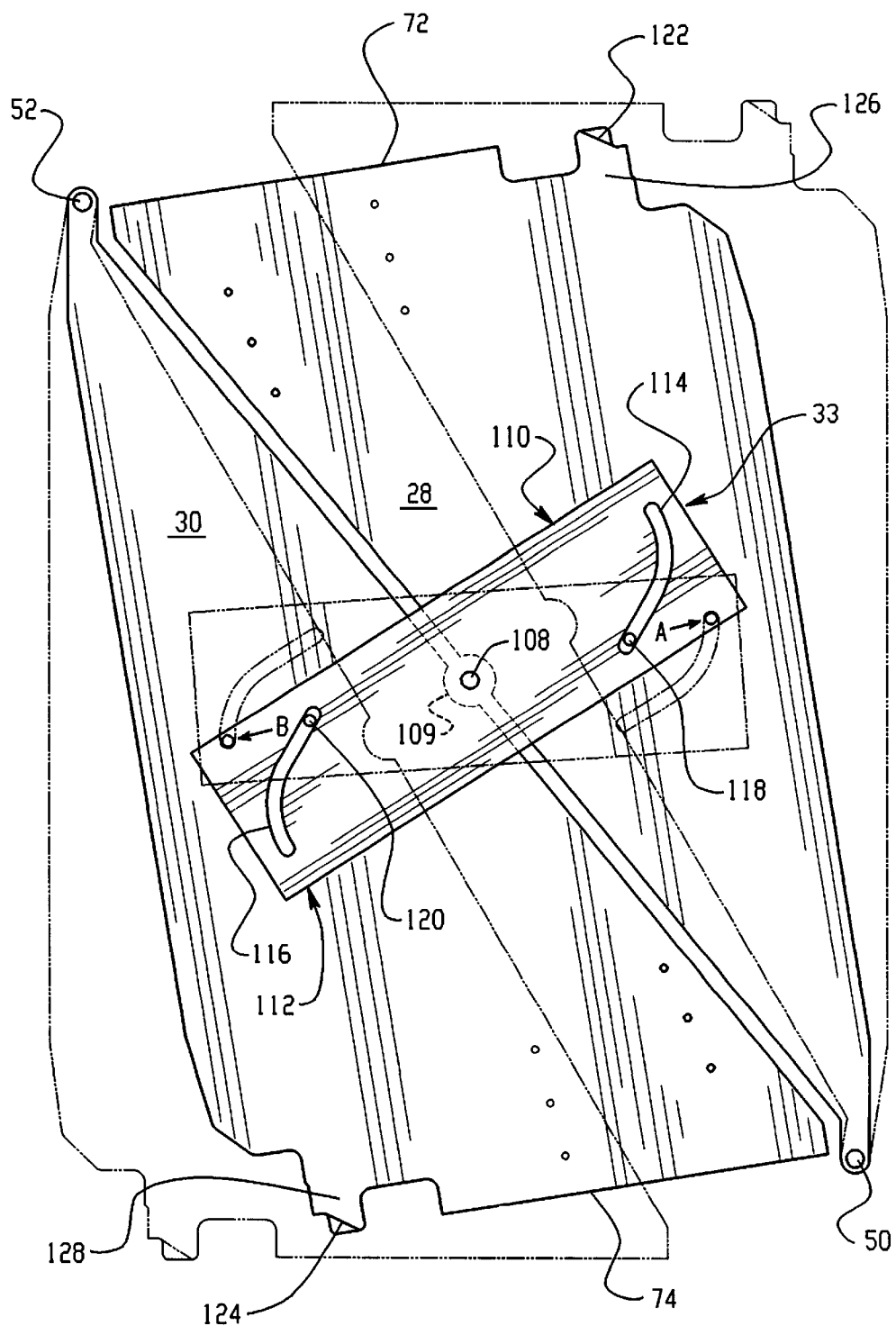

With reference to FIG. 7, one preferred embodiment of the coupling member 33 is shown. It is to be appreciated, however, that a variety of mechanisms for articulating the plates 28 and 30 to the engaged positions are also contemplated, which may include separate mechanisms for moving each of the plates. The coupling member 33 provides a convenient means for rotating the heavy plates with a minimum of rotational force. The coupling member preferably defines a flat rectangular plate, and may be formed from steel or other rigid material. It is pivotally connected at its center to the front face 32 of the door by an axle or shaft member 108, such as a central pivot pin. Preferably, the axle member is located in the gap between the two plates, at the geometric center of the assembly. The axle member allows the coupling member to rotate in a plane parallel to the front face 32 of the door. Each of the plates 28, 30 may define a semi-circular cut-out portion 109 adjacent the central pivot pin 108 so that the plates do not obstruct rotation of the central pivot pin.

A first, or upper portion 110 of the coupling member 33 overlaps the upper plate 28 while a second, or lower portion 112 of the coupling member overlaps the lower plate 30. First and second curved cam slots 114 and 116 are defined in the first and second portions 110 and 112, respectively. First and second low friction shafts or pins 118 and 120, are connected with the plates 28 and 30, respectively. The shafts extend outwardly from the plates and are received through the cam slots 114 and 116. In cooperation, the coupling member 33, the pivot pins 50 and 52, and the shafts 118 and 120 maintain the plates 28 and 30 in close proximity to the front face 32 of the door, particularly when the plates are in the disengaged position. Other devices may also be added to maintain close proximity.

The cam slots 114 and 116 are configured such that, in the disengaged position, the first shaft 118 is located adjacent a lower end of the first cam slot 114 while the second shaft 120 is at an upper end of the second cam slot 116. The positions of the shafts and the cam slots are reversed in the engaged position, with the first shaft 118 being cammed to the upper end of the first cam slot 114 and the second shaft 120 being cammed to the lower end of the second cam slot 116. To reduce friction between the shafts 118 and 120, and resulting wear of the shafts, the shafts optionally include an outer layer of a low friction material, such as a sleeve of TEFLON. Alternatively, the shafts include a rotatable outer portion, such as a sleeve, which is spaced from the shaft by bearings.

The coupling member may be moved manually, by an operator, between the disengaged and engaged positions, or be power operated. Preferably, a handle, such as a wheel or crank, is connected to the coupling member 33 to rotate it between its two positions. As the force is applied, the coupling member 33 rotates in a clockwise direction around the central pivot pin 108, and the two plates 28 and 30 are rotated clockwise around their respective pivot pins So and 52, into the engagement positions.

The plates 28, 30 are mutually counterbalanced around the coupling member. Specifically, the upward force required to push the upper plate 28 into the engaged position is generally counterbalanced by the downward force of the lower plate 30 which tends to pull the lower plate to the engaged position.

The two spacer plates 28 and 30 are bound to follow the cam slots 114 and 116 of the rotating coupling member 33. To maintain counterbalancing, i.e., for the plates to remain at rest in any position, or, alternately, to take zero torque to rotate the coupling member to actuate the plates, the net torque on the coupler should remain zero. Taking moments about the coupling member pivot point 108, there are only two forces—the contact at the two cam surfaces. In order for them to equal zero, the cross product of the force and location vector for each contact is equal and opposite.

By hanging the plates 28 and 30, with one naturally wanting to rotate to the disengaged position while the other naturally wanting to rotate to the engaged position, by making them identical, so that the weight of each is the same and, just as importantly, the horizontal distance from the plate's center of gravity to the pivot point of each identical at any position, and by making the cam slots mirrors so that the direction of the force vector to the coupler is identical for each plate, the net torque on the coupler remains zero. It should be appreciated that an equivalent counterbalancing could be achieved by shaping each plate differently or pivoting the plates about non-mirrored points, and maintaining a zero net torque by altering the shape of the cam slots.

Additionally, only a small amount of articulation, preferably from about 5–10°, and more preferably about 7°, brings the plates to the engaged position. Accordingly, only a small net force to overcome friction forces is supplied by the operator to move the plates.

To return the plates 28 and 30 to the disengaged position, the movements are reversed. The operator applies a small counterclockwise torque on the coupling member 33 camming the shafts 118, 120 inward toward each other.

The cam slots 114 and 116 are configured to cam the shafts smoothly such that when the plates 28 and 30 are in the engagement position, the plates 28 and 30 cannot be rotated by themselves to the disengaged position without rotating the coupling member 33. This prevents inadvertent disengagement of the plates by any rotational force which may act on the plates.

In the embodiment of FIG. 7, the engagement portions 72 and 74 of the plates 28 and 30 each define a camming surface 122 and 124, respectively, on a leading portion 126, 128, respectively, of the engagement portion. The camming surfaces are the first parts of the engagement portions to engage the corresponding retainer bars 80, and 82, respectively, when the plates are moved towards the engagement position. As the camming surface slides against the inner surface 100 of the retaining bar flange, the plate is smoothly guided into closer proximity with the outer face 32 of the door so that the remainder of the engagement portion engages the flange 92 smoothly.

To sterilize or disinfect items, the items are first loaded into the chamber 12 through the opening 16. The door 14 is then pivoted into a position where it covers the opening. The plates 28 and 30 are pivoted from the disengaged to the engaged position. The seal 96 is activated, pushing the engagement portions 72, 74, 76, and 78 into intimate engagement with the corresponding flanges 92 and sealing the interior surface of the door to the door frame 26.

At one or more stages of a sterilization or disinfection cycle, steam is admitted to the chamber under pressure to sterilize the items. The added pressure within the chamber provides an outward force on the door 14 and on the plates 28 and 30. The flanges 92 resist the outward motion of the door by limiting outward movement of each of the plates along two adjoining edges of the plate. The force on one engagement portion tending to pivot the plate outwardly is thus resisted by an opposing force on the adjacent engagement portion.

At various stages of the sterilization or disinfection cycle, the chamber is evacuated by connecting a source of vacuum, such as a vacuum pump, to the chamber. The reduced pressure within the chamber tends to draw the door 14 towards the door frame 26. The spacer portions 90 provide the door with some freedom of movement, allowing the engagement portions to move inwardly and outwardly a small amount in response to the changing pressure within the chamber.

At the end of the sterilization or disinfection cycle, the pressure within the chamber is returned to ambient pressure. The seal is deactivated by venting and/or evacuating the steam from within the seal and the plates 28, 30 are pivoted from the engaged to the disengaged position. The door is then opened and the sterilized or disinfected items removed.

The closure assembly 20 has been described with reference to a sterilizer door. It should be understood that the closure assembly is equally suited to selectively engaging a variety of doors across an opening to a chamber, in particular, doors which are subjected to high pressures from within the chamber.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A steam sterilizer apparatus comprising:
   a pressure chamber;
   a door frame which defines an opening into the chamber;
   a rectangular door connected to the door frame, the door being sized to cover the opening and having four edges;
   four flanges connected with the door frame, at least one flange being adjacent each of opposite edges of the door; and,
   a closure assembly which selectively maintains the door in a proximate relationship to the frame, the closure assembly including:
      a first plate, an uppermost portion of which is pivotally connected to the door, the first plate defining a first engagement portion which is pivoted into and out of engagement with a first of the flanges, and a second engagement portion which is pivoted into and out of engagement with a second of the flanges, and
      a second plate, a lowermost portion of which is pivotally connected to the door, the second plate defining a third engagement portion which is pivoted into and out of engagement with a third of the flanges, and a fourth engagement portion which is pivoted into and out of engagement with a fourth of the flanges.

2. The apparatus of claim 1, further including:
   a coupling member which couples the first plate to the second plate for selectively pivoting the first and second plates between a disengaged position, in which the engagement portions are displaced from the flanges, and an engagement position, in which the engagement portions engage the flanges.

3. The apparatus of claim 1, wherein the first plate defines an L-shaped peripheral edge and the second plate defines an L-shaped peripheral edge, a longer leg of the first plate L-shaped edge being positioned opposite to a longer leg of the second plate L-shaped edge and a shorter leg of the first plate L-shaped peripheral edge being positioned opposite to a shorter leg of the second L-shaped edge, the first engaging portions of the first and second plates being defined along one of the opposing longer and shorter legs.

4. The apparatus of claim 3, wherein:
   the longer and shorter legs of each plate are defined at right angles to each other;
   engagement portions are defined along both the longer and shorter legs; and,
   there are flanges disposed along four edges of the door.

5. The apparatus of claim 3, wherein:
   the first plate is pivotally connected adjacent an end of the longer leg furthest from the shorter leg; and,
   the second plate is pivotally connected adjacent an end of the longer leg farthest from the shorter leg.

6. A steam sterilizer apparatus comprising:
   a pressure chamber;
   a door frame which defines an opening into the chamber;
   a door connected to the door frame, the door being sized to cover the opening;
   a plurality of flanges connected with the door frame, at least one flange being adjacent each of opposite edges of the door; and,
   a closure assembly which selectively maintains the door in a proximate relationship to the frame, the closure assembly including:
      a first plate, an uppermost portion of which is pivotally connected to the door, the first plate defining at least a first engagement portion which is pivoted into and out of engagement with a first of the flanges,
      a second plate, a lowermost portion of which is pivotally connected to the door, the second plate defining at least a first engagement portion which is pivoted into and out of engagement with a second of the flanges,
      a rotatable coupling member which couples the first plate to the second plate for selectively pivoting the first and second plates between a disengaged position, in which the engagement portions are displaced from the flanges, and an engagement position, in which the engagement portions engage the flanges, the coupling member defining a first arcuate slot therein and a second arcuate slot therein, a first follower connected at a first end to an outer surface of the first plate and extending into the first slot, and a second follower connected at a first end to an outer surface of the second plate and extending into the second slot;

whereby the plates are rotated into and out of the engaged position in concert and the followers move oppositely along the slots, as the coupling member rotates.

7. The apparatus of claim 6, further including:

a channel defined in the door frame around the opening; and, a sealing member received in the channel, the sealing member selectively sealingly engaging an interior surface of the door when the door is in the engaged position.

8. A steam sterilizer apparatus comprising:

a pressure chamber;

a door frame which defines an opening into the chamber;

a door connected to the door frame, the door being sized to cover the opening;

a plurality of flanges connected with the door frame, at least one flange being adjacent each of opposite edges of the door; and, a closure assembly which selectively maintains the door in a proximate relationship to the frame, the closure assembly including:

a first plate, an uppermost portion of which is pivotally connected to the door, the first plate defining at least a first engagement portion which is pivoted into and out of engagement with a first of the flanges, a second plate, a lowermost portion of which is pivotally connected to the door, the second plate defining at least a first engagement portion which is pivoted into and out of engagement with a second of the flanges, the plates being generally triangular and of the same mass and general geometry, a coupling member which couples the first plate to the second plate, such that gravitational forces on the first and second plates are counterbalanced around the coupling member, whereby as the first and second engagement portions are pivoted into engagement with the first and second flanges, the plates exert balanced opposing forces on the coupling member.

9. A steam sterilizer apparatus comprising:

a pressure chamber;

a door frame which defines an opening into the chamber;

a door connected to the door frame, the door being sized to cover the opening;

a plurality of flanges connected with the door frame, at least one flange being adjacent each of opposite edges of the door; and, a closure assembly which selectively maintains the door in a proximate relationship to the frame, the closure assembly including:

a first plate, pivotally connected to the door, the first plate defining an L-shaped peripheral edge and at least a first engagement portion which is pivoted into and out of engagement with a first of the flanges, and a second plate, pivotally connected to the door, the second plate defining an L-shaped peripheral edge and at least a second engagement portion which is pivoted into and out of engagement with a second of the flanges; and a coupling member for coordinatedly pivoting the first and second plates, the coupling member including:

a first, arcuate cam surface which engages a follower on the first plate, a second, arcuate cam surface which engages a follower on the second plate, and a rotatable mounting for the coupling member such that (1) as the coupling member rotates in one direction the cam surfaces cam the followers apart moving the engagement portions into engagement with the flanges and (2) as the coupling member rotates in an opposite direction the cam surfaces cam the followers toward each other moving the engagement portions out of engagement with the flanges.

10. An apparatus comprising:

a pressure chamber;

a door frame which defines an opening into the chamber;

a door connected to the door frame, the door being sized to cover the opening;

a plurality of flanges connected with the door frame, at least one flange being adjacent each of opposite edges of the door;

a first plate, pivotally connected to the door, the first plate defining at least a first engagement portion which is pivoted into and out of engagement with a first of the flanges;

a second plate, pivotally connected to the door, the second plate defining at least a second engagement portion which is pivoted into and out of engagement with a second of the flanges; and a coupling member for coordinatedly pivoting the first and second plates, the coupling member including:

a first, curved cam surface which engages a follower on the first plate, a second, curved cam surface which engages a follower on the second plate, the cam surfaces having an overcenter geometry which prevents the engagement portions from being moved out of engagement with the flanges unless the coupling member is rotated by an external force.

11. A closure assembly for selectively maintaining a door in sealing engagement around an opening in cabinet, four flanges extending from a front face of the cabinet adjacent the door, the assembly comprising:

a first plate which includes a first pivot point for pivotally connecting the first plate to an exterior surface of the door adjacent a first edge of the door, the first plate defining a first engagement portion for selectively engaging a first of the flanges and a second engagement portion for selectively engaging a second of the flanges, the first and second engagement portions being separated from each other by a recess;

a second plate which includes a second pivot point for pivotally connecting the second plate to the exterior surface of the door adjacent a second edge of the door, the second plate defining a third engagement portion for selectively engaging a third of the flanges and a fourth engagement portion for selectively engaging a fourth of the flanges, the third and fourth engagement portions being separated from each other by a recess; and, a coupling member which couples the first plate to the second plate for concurrently rotating the first and second plates from a disengaged position, in which the engagement portions are displaced from the flanges, to an engagement position, in which the engagement portions engage the flanges.

12. The closure assembly of claim 11, wherein the first and second plates define triangles with longest sides of the triangles being positioned in facing opposition.

13. The closure assembly of claim 12, wherein the first and second engagement portions are defined at right angles to each other and the third and fourth engagement portions are defined at right angles to each other.

14. The closure assembly of claim 12, wherein the first engagement portion is positioned further from the first pivot point than the second engagement portion, and wherein the first engagement portion includes a camming surface for camming against the first flange and wherein the third engagement portion is positioned further from the second pivot point than the fourth engagement portion, and wherein the third engagement portion includes a camming surface for camming against the third flange.

15. The closure assembly of claim 11, wherein the pivot points are positioned for pivotally connecting the first and second plates adjacent to diagonally opposite corners of the front face of the door.

16. The closure assembly of claim 11, wherein the coupling member defines a first slot and a second slot and wherein a first shaft is connected at a first end to an outer surface of the first plate and extends into the first slot and a second shaft is connected at a first end to an outer surface of the second plate and extends into the second slot;

whereby applying a rotational force to the coupling member, the plates are pivoted into and out of the engagement position.

17. The closure assembly of claim 16, wherein the coupling member defines a first slot and a second slot and wherein a first shaft is connected at a first end to an outer surface of the first plate and extends into the first slot and a second shaft is connected at a first end to an outer surface of the second plate and extends into the second slot;

whereby by applying a force to at least one of the first and second shafts, the plates are pivoted into and out of the engagement position.

18. A closure assembly for selectively maintaining a door in sealing engagement around an opening in a cabinet, the door having four sides, flanges extending from a front face of the cabinet adjacent the sides of the door, the assembly comprising:

a first plate which includes a first pivot point adjacent an uppermost corner thereof for pivotally connecting the first plate to a surface of the door, the first plate defining at least one engagement portion for selectively engaging at least one of the flanges;

a second plate which includes a second pivot point adjacent a lowermost corner thereof for pivotally connecting the second plate to the surface of the door, the first and second pivot points being diagonally opposite, the first and second plates having the same mass, the second plate defining at least one engagement portion for selectively engaging at least one of the flanges;

a coupling member disposed on a diagonal between the first and second pivot points and coupling the first plate to the second plate for concurrently rotating the first and second plates about the first and second pivot points between a disengaged position, in which the engagement portions are displaced from the flanges, and an engagement position, in which the engagement portions engage the flanges;

the plates being counterbalanced around the coupling member such that the first and second plates exert equal and opposite forces on the coupling member as the plates are rotated.

19. A method of selectively restraining a door across an opening, the method including:

pivoting a first plate which defines a first engagement portion and a second engagement portion from a first position, in which the first engagement portion is spaced from a first flange and a second engagement portion is spaced from a second flange to a second position, in which the first engagement portion engages the first flange and the second engagement portion engages the second flange, the first plate being pivotally connected to the door;

pivoting and a second plate which defines a third engagement portion and a fourth engagement portion from a first position, in which the third engagement portion is spaced from a third flange and a fourth engagement portion is spaced from a fourth flange to a second position, in which the third engagement portion engages the third flange and the fourth engagement portion engages the fourth flange, the second plate being pivotally connected to the door.

20. The method of claim 19, further including:

activating a seal around the opening to seal a space between the opening and the door.

21. The method of claim 19, wherein the steps of pivoting the first plate and pivoting the second plate include:

pivoting the first plate about a bottom corner of the door and the second plate about an opposite upper corner of the door; and, coupling the first and second plates such that the plates are pivoted coordinately, such that as the plates are pivoted apart toward the engagement position, the gravitational forces on the two doors counterbalance.

22. The method of claim 19 further including:

applying a vacuum pressure to the interior of the door; and, applying a steam pressure to an interior surface of the door, the flanges cooperating to maintain the door in a sealing relationship around the opening.

* * * * *